(12) United States Patent
Joens et al.

(10) Patent No.: US 8,852,421 B2
(45) Date of Patent: Oct. 7, 2014

(54) CONVERTER FOR USE WITH SENSING DEVICES

(75) Inventors: Michael Joens, Beverly, MA (US); Ricky F. Baggio, Waltham, MA (US)

(73) Assignee: EMD Millipore Corporation, Billerica, MA (US)

( * ) Notice: Subject to any disclaimer, the term of this patent is extended or adjusted under 35 U.S.C. 154(b) by 88 days.

(21) Appl. No.: 13/334,592

(22) Filed: Dec. 22, 2011

(65) Prior Publication Data
US 2012/0091012 A1  Apr. 19, 2012

Related U.S. Application Data

(62) Division of application No. 12/730,754, filed on Mar. 24, 2010.

(60) Provisional application No. 61/169,415, filed on Apr. 15, 2009.

(51) Int. Cl.
| | | |
|---|---|---|
| G01F 1/64 | (2006.01) | |
| G01N 17/00 | (2006.01) | |
| G01N 27/26 | (2006.01) | |
| G01N 21/66 | (2006.01) | |
| G01N 21/64 | (2006.01) | |

(52) U.S. Cl.
CPC ........ G01N 21/66 (2013.01); *G01N 2021/6432* (2013.01)
USPC ......... 205/782; 205/785; 204/406; 204/228.1

(58) Field of Classification Search
USPC ................. 205/785; 204/228.1, 228.6, 229.1
See application file for complete search history.

(56) References Cited

U.S. PATENT DOCUMENTS

| | | |
|---|---|---|
| 4,742,808 A | 5/1988 | Blumel et al. |
| 5,312,528 A | 5/1994 | Hoogendijk |

(Continued)

FOREIGN PATENT DOCUMENTS

| | | |
|---|---|---|
| JP | 5-334587 A | 12/1993 |
| JP | 8-287346 A | 11/1996 |

(Continued)

OTHER PUBLICATIONS

Kong et al (Cytotechnology vol. 16 pp. 227-236, 1998) as provided on IDS dated Feb. 17, 2012.*

(Continued)

*Primary Examiner* — Luan Van
*Assistant Examiner* — Louis Rufo
(74) *Attorney, Agent, or Firm* — Nields, Lemack & Frame, LLC (57) ABSTRACT

A system and method are disclosed for utilizing sensors with existing devices. An interface module is used in combination with a newer sensor, such as a fluorescence oxygen sensor, and an older legacy device. The older legacy device supplies a polarizing voltage, and anticipates a measured current of between 0 and 100 nA. The newer sensor requires no polarizing voltage and delivers an output of 0-10 volts in one embodiment, and 4-20 mA in another embodiment. The interface module receives the output from the sensor, and converts it into a useable signal to the legacy device. In another embodiment, the interface module comprises a number of outputs, such that both legacy devices and newer devices can be in communication with the sensor simultaneously. The interface module can be used in conjunction with a reactor chamber or other pharmaceutical process.

11 Claims, 6 Drawing Sheets

(56) References Cited

U.S. PATENT DOCUMENTS

| | | | |
|---|---|---|---|
| 5,326,447 | A * | 7/1994 | Fletcher .................. 205/782.5 |
| 5,344,544 | A | 9/1994 | North et al. |
| 5,669,009 | A | 9/1997 | Buktenica et al. |
| 5,708,368 | A | 1/1998 | Mallory |
| 5,735,605 | A | 4/1998 | Blalock |
| 5,793,230 | A | 8/1998 | Chu et al. |
| 5,854,731 | A | 12/1998 | Thomas |
| 6,188,340 | B1 * | 2/2001 | Matsumoto et al. .......... 341/110 |
| 6,954,407 | B1 | 10/2005 | Gleim |
| 6,960,290 | B2 | 11/2005 | Akhavan et al. |
| 7,135,841 | B1 | 11/2006 | Tomiyoshi et al. |
| 7,433,267 | B2 | 10/2008 | Murphy et al. |
| 2002/0098120 | A1 | 7/2002 | Blazewicz et al. |
| 2004/0160277 | A1 | 8/2004 | Cerisola |
| 2005/0066084 | A1 * | 3/2005 | Benninger ..................... 710/62 |
| 2007/0035410 | A1 | 2/2007 | Cohen et al. |
| 2010/0264041 | A1 | 10/2010 | Joens et al. |

FOREIGN PATENT DOCUMENTS

| | | |
|---|---|---|
| JP | 9-282271 A | 10/1997 |
| JP | 2004-536307 A | 12/2004 |
| JP | 2005-252810 A | 9/2005 |
| JP | 2007-198735 A | 8/2007 |
| WO | 03/008957 A1 | 1/2003 |

OTHER PUBLICATIONS

Product Documentation for Yokogawa DO402G.*

Product Documentation for Yokogawa MXD.*

Extended European Search Report and Written Opinion dated Jun. 27, 2011 in corresponding foreign patent application No. EP 10158880.4.

PreSens-O2-Fibox 3 & Fibox 3-trace Info Sheet, 2006, "Single-channel oxygen transmitters Temperature compensated system", 2 pages.

Broadley-James Corporation, Summer 1998, Precision Sensor News, "An OxyProbe Success Story" article, 3 pages.

PreSens Precision Sensing Delivery Note dated Nov. 22, 2005, Project No. 115, Document 2005-20159, 1 page.

PreSens Precision Sensing Delivery Note dated Aug. 2, 2006, Project No. 882, Document 2006-20751, 2 pages.

PreSens Precision Sensing GmbH Instruction Manual, FIBOX 3-LCD Fiber-Optic Oxygen Meter, Software Version LCDPST3v103, May 2004, 101 pages, Dr. Huber, et al.

PreSens Precision Sensing GmbH "Fibox 3 LCD-trace Single Channel Fiber-Optic Oxygen Meter for Minisensors" Infomation Sheet, Jul. 26, 2006, 17 pages, Dr. Huber.

Reichert & Kollegen communication re: US Patent Application 2010/0264041, dated Jul. 12, 2011, 1 page.

Cytotechnology, vol. 26, No. 3, Mar. 1, 1998, pp. 227-236, XP 019236538, "Development of a versatile computer integrated control system for bioprocess controls", Kong, et al.

Measurement Science and Technology, vol. 18, No. 10, Oct. 1, 2007, pp. 3177-3186, XP 020118438, "Optical fibre biosensors using enzymatic transducers to monitor glucose", Scully, et al.

Office Action mailed Jan. 5, 2012 in corresponding U.S. Appl. No. 12/730,754.

Advantech Co., Ltd., Product documentation provided from Advantech for PCL-818L multifunction card, 2 pages, date unknown, admitted prior art.

Sensors and Actuators A: Physical, vol. 91, Issues 1-2, Jun. 2001, pp. 12-15, "Integrated Online Diagnosis for AMR-based Angular Measurement Systems", Dietmayer, 5 pages.

Japanese Communication mailed Jul. 31, 2012 in corresponding Japanese Patent Application No. JP 2010-094162.

Chinese Communication issued Jul. 16, 2012 in corresponding Chinese Patent Application No. CN 201010165243.2.

Final Rejection mailed Jul. 25, 2012 in corresponding U.S. Appl. No. 12/730,754.

Applicant-Initiated Interview Summary, mailed Sep. 11, 2012 in corresponding U.S. Appl. No. 12/730,754.

Yokogawa Electric Corporation, Yokogawa Model MXD product documentation, GS 77 J04X12-01E, 6 pages, Nov. 2005.

Office Action mailed Oct. 24, 2012 in corresponding U.S. Appl. No. 12/730,754.

Final Rejection mailed Jun. 5, 2013 in corresponding U.S. Appl. No. 12/730,754.

Notice of Allowance mailed Jul. 30, 2014 in corresponding U.S. Appl. No. 12/730,754.

* cited by examiner

CONVERTER FOR USE WITH SENSING DEVICES

This application is a divisional application of U.S. patent application Ser. No. 12/730,754, filed Mar. 24, 2010, which claims priority of U.S. Provisional Patent Application No. 61/169,415, filed Apr. 15, 2009, the disclosures of which is incorporated herein by reference in their entirety.

BACKGROUND OF THE INVENTION

Many industries, such as the pharmaceutical industry, employ sensing devices to monitor the progress or outcome of a particular event. Often, these sensing devices are used to provide input to a controller, which then varies its output, based on this input. The output of the controller is typically used to influence, affect or control the particular event.

For example, in a bioreaction, it may be important to monitor and control a number of characteristics of the reaction, including but not limited to temperature, pH, oxygen concentration, or other parameters. Because of this, devices have been developed to sensor these characteristics. There exists a plethora of pH sensors, dissolved oxygen sensors and temperature sensors.

Figure 1:
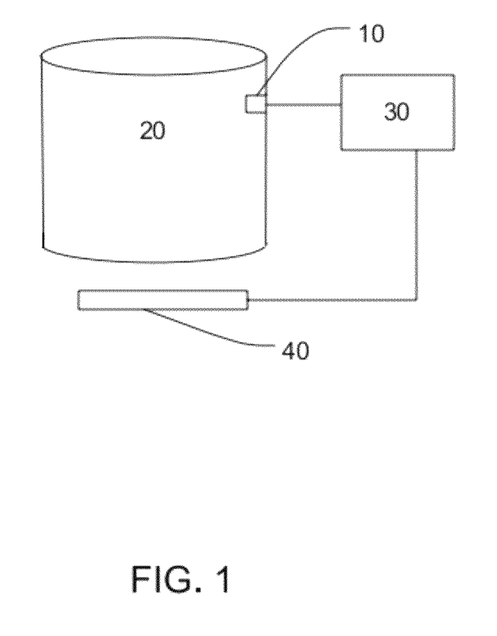
FIG. 1 illustrates a simple control system.

However, while sensing the characteristic is important, it is equally important to be able to monitor and track these characteristics over time. Additionally, it is important to use these characteristics to determine future actions. For example, FIG. 1 shows a simple example of a closed loop control system which can be used with a bioreactor. In this figure, a temperature sensor 10 may be used to monitor the temperature of a particular reaction occurring within a reaction chamber 20. Based on the output of the temperature sensor 10, a controller 30, in communication with that sensor 10, may vary the output of a heating element 40. In this way, if the temperature within the reaction chamber must be within a prescribed temperature range, the controller 30 can use the sensor 10 and the heating element 40, in conjunction with a software control loop, to insure that these conditions are met.

Additionally, the sensor 10 may be in communication with other devices. For example, the output of a pH sensor may be in communication with controller, a logging device and/or data storage device. The attached device samples the output of the specific sensor over time. This sampling step may be performed periodically, such as at fixed time intervals. In other embodiments, this sampling step is performed at sporadic intervals, or based on other external events.

In the case of a data logger, the value sampled is simply stored, usually with an associated timestamp, so that a graph of that characteristic over a period of time can be generated. In the case of the controller, the value is sampled so that corrective action can be performed. For example, as described above, in the case of a temperature sensor, the controller may be in communication with a heating element, such that if the temperature reading is below a predetermined threshold, the controller actuates the heating element. Similar actions can be taken in response to pH or dissolved oxygen readings.

Figure 2:
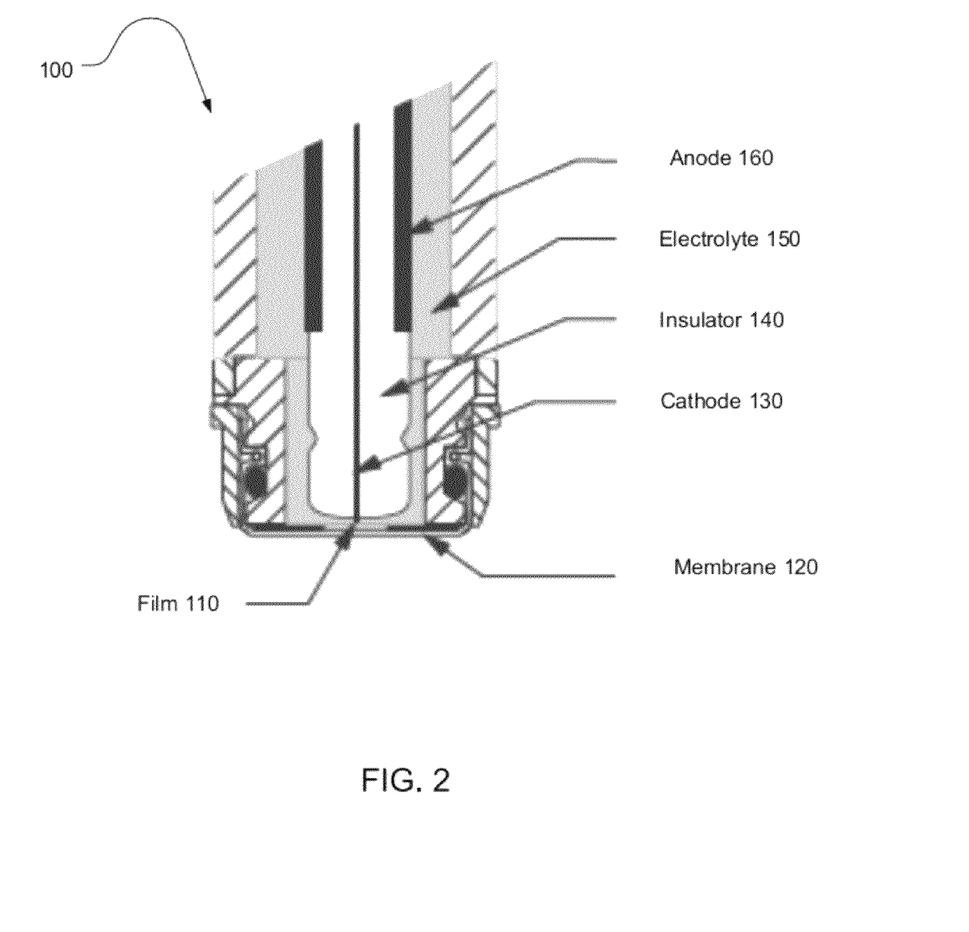
FIG. 2 is a representative cross section of a polarographic oxygen sensor of the prior art.

One of the most common dissolved oxygen sensor is known as a polarographic sensor. A representative sensor is shown in FIG. 2. The sensor 100 includes a membrane 120 through which oxygen can pass. It also includes a cathode 130 and an anode 160. In some embodiments, the cathode 130 is made from a conductive material, such as platinum. In some embodiments, the anode 160 is made from a conductive material, such as gold or silver. These two conductive components are separated by an insulator 140, such as glass. An external device provides a voltage potential, such as between 600 and 800 mV, between the cathode 130 and the anode 160.

In operation, oxygen molecules diffuse through the membrane 120. These molecules are reduced at the surface of the cathode 130, such as according to the following equation:

$$O_2 + 2H_2O + 4e^- \rightarrow 4OH^-$$

At the anode, an oxidation reaction is occurring, thereby producing electrons. These electrons move toward the cathode 130, thereby generating a current proportional to the oxygen concentration. This current can then be measured by a device, such as a controller or a logging device.

Because of the popularity of polarographic sensors, many devices, such as controllers, including those made by Applikon, were designed to interface directly to them. In other words, these devices, provided a polarizing voltage of 600-800 mV, and were designed to measure the resulting current flow, which is in the range of 0-100 nA. These devices also were used to control operations, such as bioreactions, and have been used for a significant amount of time. Thus, there exists a large installed base of these controllers and other devices, configured to interoperate with polarographic sensors.

More recently, alternative sensors have been developed. Unlike traditional polarographic sensors, these alternative sensors typically use a different indicator of oxygen content. One such indicator is fluorescence. In one embodiment, the sensor has an emitter, which emits light, typically at a specific wavelength, such as 475 nm. The light is directed toward a sensing element. The sensing element has a thin layer of hydrophobic material. A compound capable to fluorescing, such as ruthenium, is trapped within the hydrophobic material, effectively shielded from the water. The light excites the ruthenium, which then emits energy at a specific wavelength, such as 600 nm.

Oxygen is able to effectively quench the fluorescence of ruthenium. Collision of an oxygen molecule with a fluorophore in its excited state leads to a non-radiative transfer of energy. Thus, the more collisions that occur, the less fluorescence is created. The frequency of collisions is directly related to the concentration of oxygen molecules. Therefore, the measured fluorescence is a direct measure of the concentration of oxygen molecules.

These sensors are typically more accurate than traditional polarographic sensors. Furthermore, since they do not include any precious metals, such as platinum and silver, they are typically much less expensive. These qualities make these newer sensors the preferred choice in many applications. For example, disposable systems are more likely to utilize fluorescence oxygen sensors, due to the lower cost (especially when taking into account that the sensor will be discarded with the bag).

However, today, it is not possible to use these new sensors with existing systems. Unlike polarographic sensors, this optical-based sensors do not require a polarizing voltage input. Furthermore, rather than producing a very small current, the output of an optical-based oxygen sensor is typically between 0 and 10 volts. In another embodiment, the output is typically between 4 and 20 mA. These outputs are completely incompatible with the input characteristics of existing devices, such as Applikon controllers. Therefore, the adoption of these new optical-based sensors has been slowed.

Therefore, it would be beneficial if there were a system and method whereby these new, inexpensive, accurate oxygen sensors can be employed with existing devices, such as data loggers and controllers. Furthermore, it would be advantageous if these sensors were compatible with both older legacy controllers, and newer devices, such that two devices, such as a data logger and a controller, can be used simultaneously.

SUMMARY OF THE INVENTION

The problems of the prior art are alleviated by the system and method disclosed herein. An interface module is used in combination with a newer sensor, such as a fluorescence oxygen sensor, and an older legacy device. The older legacy device supplies a polarizing voltage, and anticipates a measured current of between 0 and 100 nA. The newer sensor requires no polarizing voltage and delivers an output of 0-10 volts in one embodiment, and 4-20 mA in another embodiment. The interface module receives the output from the sensor, and converts it into a useable signal to the legacy device. In another embodiment, the interface module comprises a number of outputs, such that both legacy devices and newer devices can be in communication with the sensor simultaneously.

DETAILED DESCRIPTION OF THE INVENTION

Pharmaceutical and biological processes often involve the transformation of materials into a final product, wherein the materials undergo various reactions. Often, it is imperative to monitor these reactions, and control them, using parameters such as temperature, pH, oxygen concentration, and others. To do so, sensors are incorporated into the reaction chambers, so that the sensor can obtain and transmit information related to a particular characteristic of the reaction. These reaction chambers can be of any type, including vats and disposable plastic bags.

Figure 3:
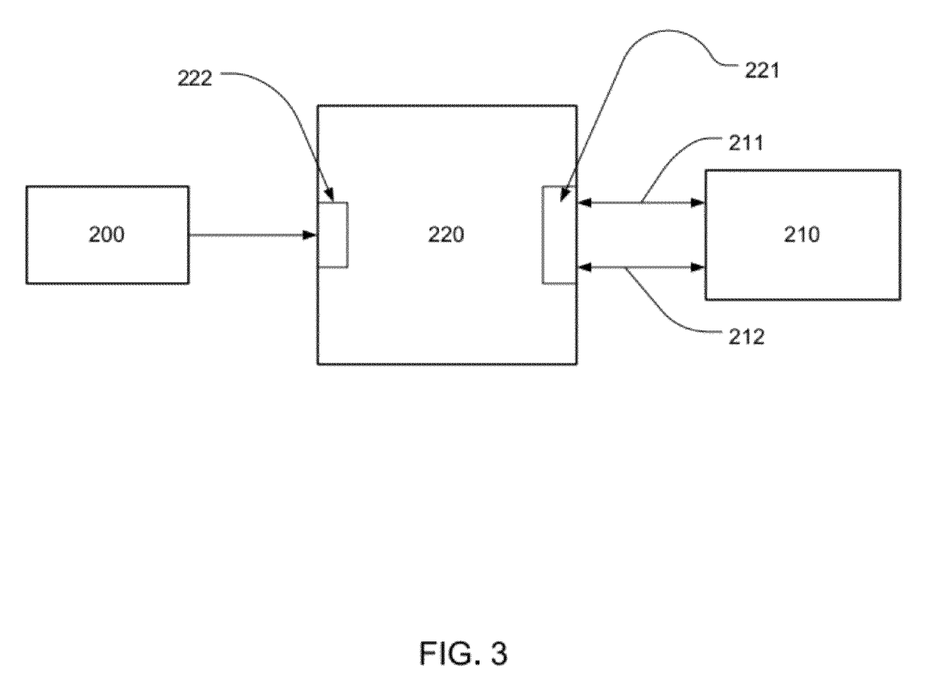
FIG. 3 is a schematic drawing of first embodiment.

FIG. 3 shows a first embodiment of the present invention. As described above, sensors, such as fluorescence oxygen sensors, produce an output that represents a measure of the characteristic that they are sensing. For example, for a fluorescence oxygen sensor, this output may be, in some embodiments, between 0 and 10 volts. In other embodiments, this output is between 4 and 20 mA. However, the specific output range and type is not important; other output ranges are within the scope of the invention.

Sensor 200 is such a sensor, having an exemplary output of 0 to 10V. This sensor 200 is to be connected to device 210. As described above, older legacy devices have certain expectations or specifications for the attached sensor. In some embodiments, the device 210 provides a polarization voltage of between 600 and 800 mV between its two leads 211,212. The output of the sensor is expected as a current between the two leads. In some embodiments, this current is between 0 and 100 nA.

Due to the difference in specifications between the sensor 200 and device 210, these two components cannot be connected directly together. Therefore, an interface module 220 is placed between the two components. This interface module 220 has an input port 222, adapted to receive signals conforming to a first specification from the sensor 200, and has an output port 221, adapted to generate outputs conforming to a second specification to the device 210. In one embodiment, the first specification is 0-10 volts. In a second embodiment, the first specification is 4-20 mA. The second specification, in one embodiment, is 0-100 nA between lead 211 and 212, with a polarizing voltage of 600 to 800 mV.

The system shown in FIG. 3 can be used with a fluorescence oxygen sensor, and a legacy controller, such as from Applikon. This system enables a variety of new configurations. In one embodiment, a disposable pharmaceutical system can be used. Such a system may include disposable storage bags, reaction bags and filtering devices. To reduce total product cost, it is advantageous to use fluorescence oxygen sensors, as these are less expensive than traditional polarographic sensors. However, disposable systems, much like traditional systems, need to be monitored and controlled. The inability of an existing legacy controller to operate with a fluorescence sensor thwarts the adoption of this configuration. However, the disclosed system, and specifically the inclusion of the interface module 220, enables such a disposable configuration.

In another embodiment, a traditional bioreactor can be fitted with fluorescence oxygen sensors. These sensors require less maintenance, less calibration and are more accurate than polarographic sensors. Therefore, they may be more desirable in reactions requiring precision control. The introduction of the interface module 220 allows a legacy controller 210 to be used with this bioreactor.

Figure 4:
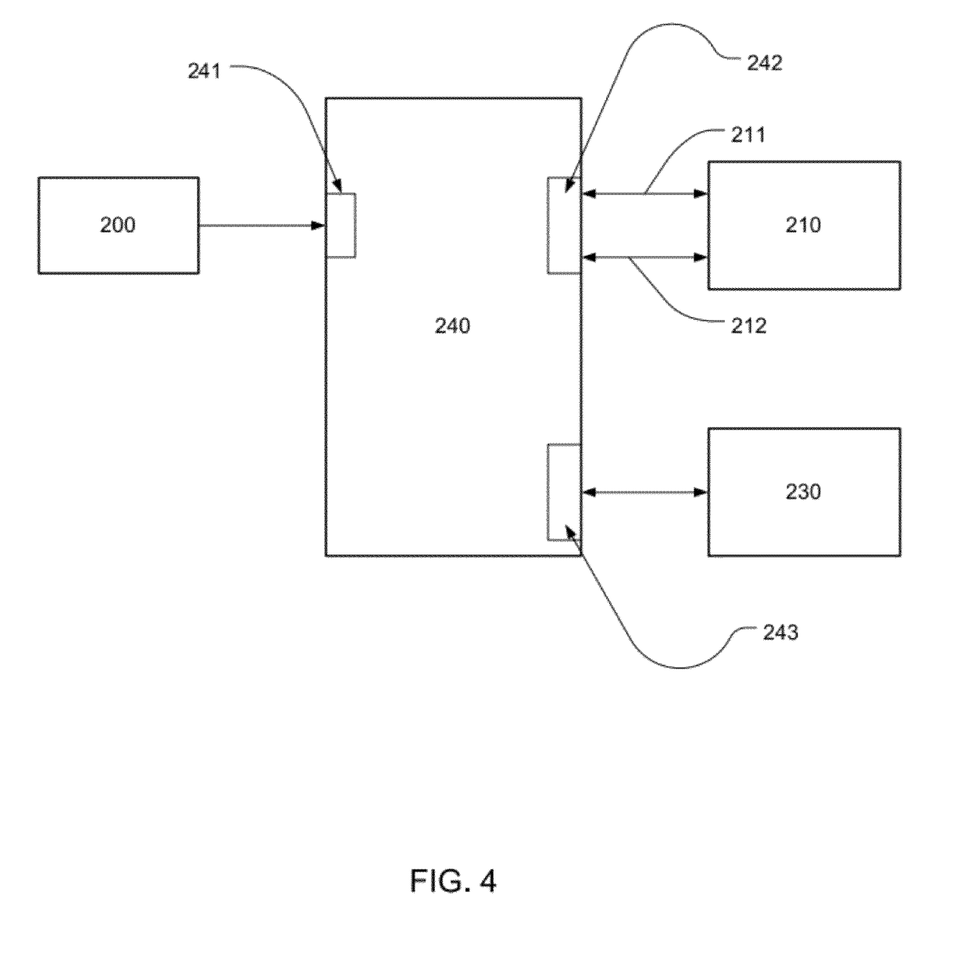
FIG. 4 is a schematic drawing of a second embodiment.

FIG. 4 shows a second embodiment of the present invention. This embodiment includes the sensor 200 and device 210. However, in this embodiment, a second device 230 is introduced.

In some embodiments, this second device 230 is adapted to receive signals conforming to the second specification. In other words, it can interface directly to the sensor 200. In this embodiment, the interface module 240 contains an input port 241, adapted to receive signals from the sensor 200. The interface module also includes the circuitry required to convert these signals from the first specification to the second specification for the first device 210. This modified output is available on port 242. The interface module 240 also includes a second output port 243 to which the second device 230 can attach. This second output port 243 simply passes the signals received at input port 241 from the sensor 200 to the second device 230. In some embodiments, the interface module may buffer this signal to reduce noise or load. One exemplary configuration may include a data logger functioning as the second device 230. This data logger may be able to accept a signal having an output between 0 and 10 V. In such a scenario, it is attached to the second port 243 on the interface module 221.

In other embodiments, this second device 230 is also a legacy device, and can only receive signals conforming to the first specification. In this embodiment, the interface module 221 contains duplicate circuitry to produce two identical outputs on output ports 242, 243 for the two devices 210, 230. One exemplary configuration may include a legacy data logger, which can only accept inputs from 0-100 nA.

In yet other embodiments, this second device 230 requires inputs conforming to a third specification. In this scenario, the interface module 240 may include circuit to convert input signals received on input port 241 to output signals of a third specification on output port 243.

Figure 5:
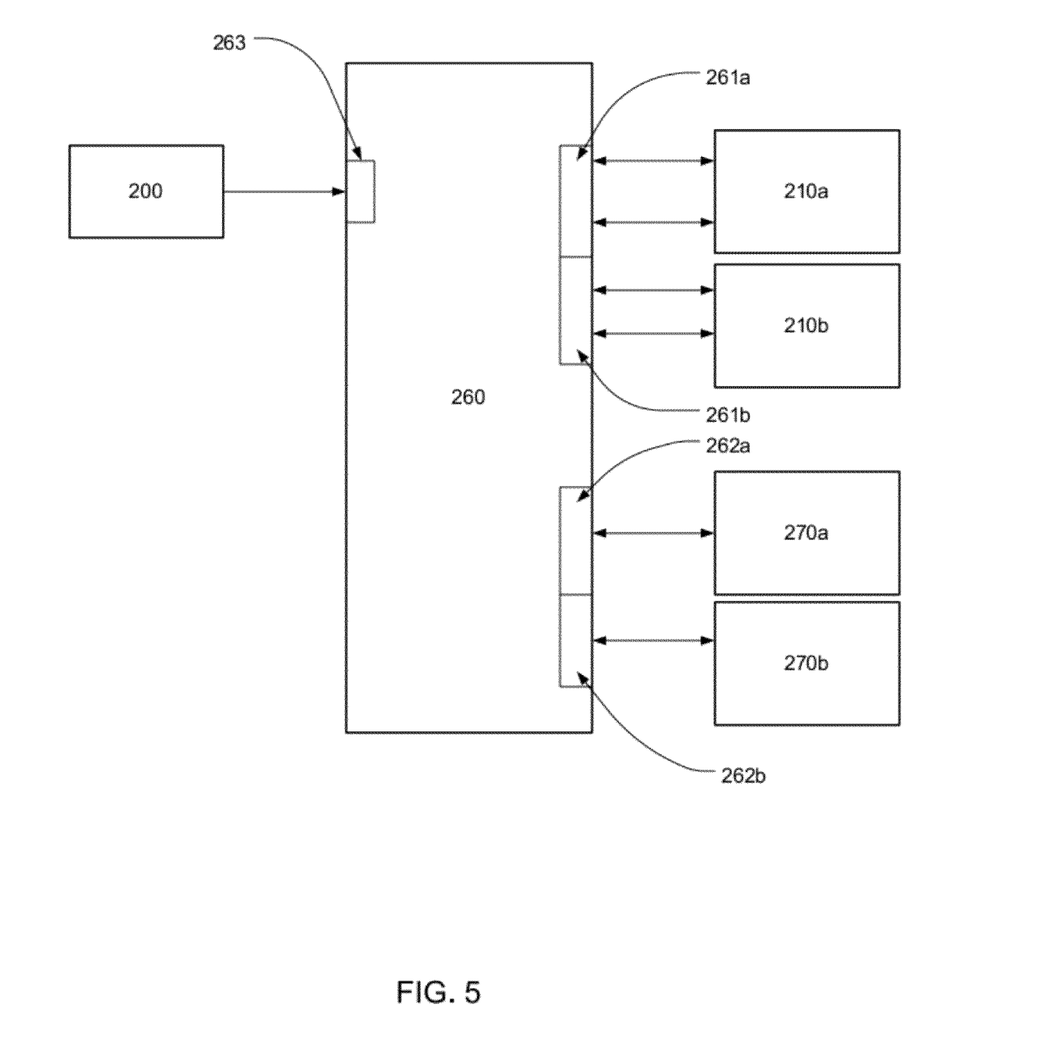
FIG. 5 is a schematic drawing of a third embodiment.

In a third embodiment, shown in FIG. 5, the interface module 260 has a plurality of output ports, where one or more output ports 261*a,b* conform to the first specification, and one or more output ports 262 *a,b* conform to the second specification. FIG. 4 shows two legacy controllers 210a,b and two other devices that conform to the second specification 270a,b. However, the number of each type of device is not limited, and all configurations of devices are within the scope of the invention.

Figure 6:
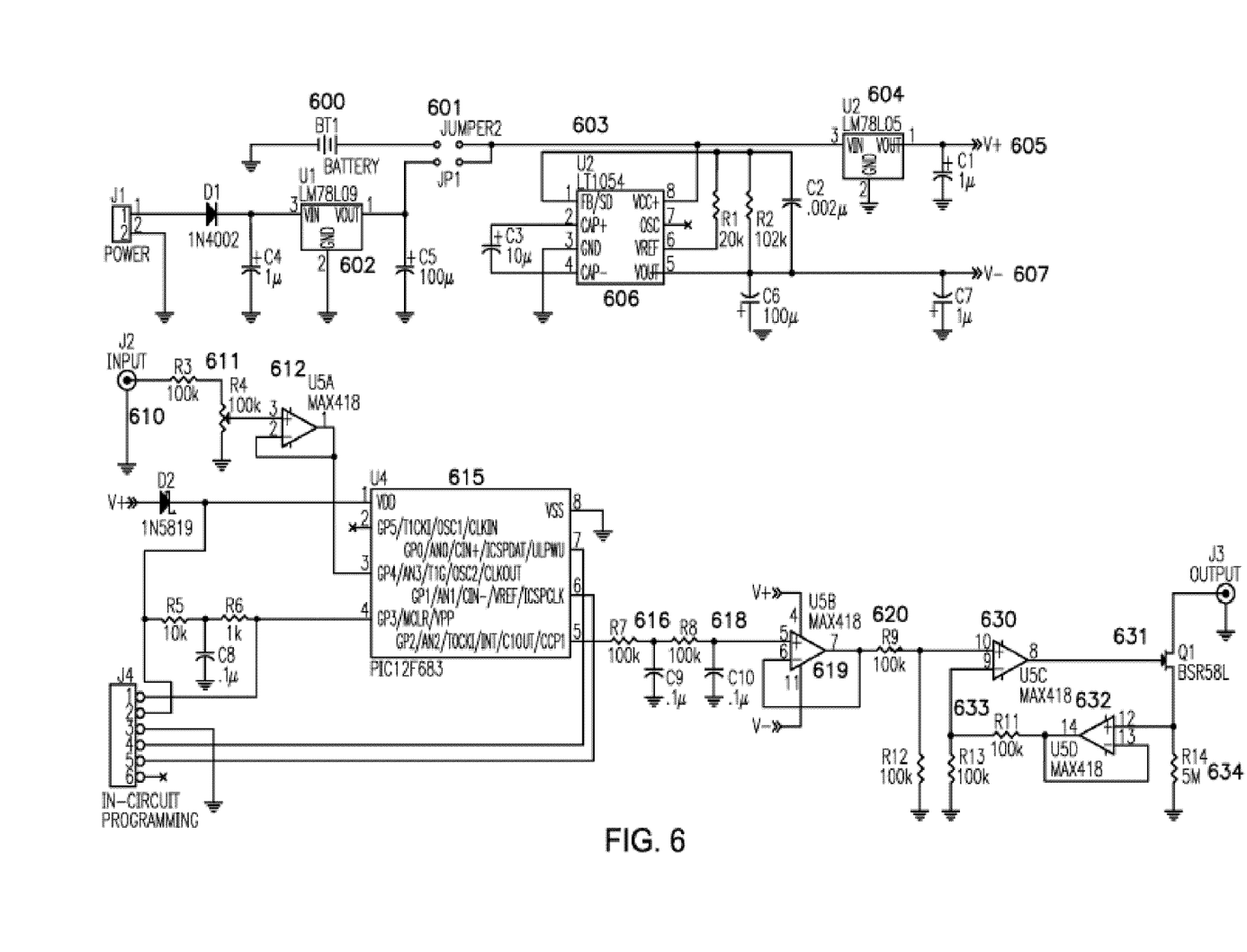
FIG. 6 is a schematic drawing of a representative circuit used in the present invention.

FIG. 6 shows a schematic of a representative circuit used to convert signals from a first specification to a second specification. In this embodiment, signals received by the interface module are in the range of 0-10 V, and the outputs must be between 0-100 nA (with a 600-800 mV polarizing voltage).

Referring to the upper portion of the Figure, the power supplies for the circuit are created, using traditional components and circuitry. The power for the interface module can be supplied either by a battery 600 or a remote power supply (not shown). The selection of the power source is performed using traditional methods, such as jumper 601. In some embodiments, the remote power source is at a voltage greater than required. In such a scenario, a voltage regulator 602 may be used to convert the incoming voltage to a lower level. The interim voltage 603 is used to create the power rails. In some embodiments, a linear regulator 604 is used to create a smooth output voltage 605. In some embodiments, a switching regulator 606 is used to create a negative rail voltage 607. Other methods of creating the necessary voltages for the interface module are well known and are within the scope of the disclosure.

A connector 610 is used to connect the output of the sensor to the interface module. In some embodiments, the output of the sensor is a voltage, in the range from 0-10 volts. In such an embodiment, a resistor divider 611 may used to reduce the voltage such that it is less than the voltage rail 605. In some embodiments, an op amp 612 is used to buffer the incoming signal so as to minimize the current load thereon. In other embodiments, the output of the sensor may be a current in the range from 4-20 mA, although other ranges are also possible and within the scope of the invention. In such an embodiment, a resistor, or resistor divider network, may be used to convert this current output to a voltage.

In certain embodiments, a programmable microprocessor, having an analog to digital (A/D) converter, and a pulse width modulated (PWM) output is used. In other embodiments, other forms of D/A conversion can be employed. The microprocessor may also have a storage element for storing code, tables or software to be executed. The microprocessor may also have RAM, which can be rewritten to serve as temporary storage. In the embodiment shown in FIG. 6, the buffered input signal 613 is connected to the internal A/D converter of programmable microprocessor 615. The microprocessor 615 converts this analog voltage to a digital value, representative of the received analog voltage. Once this is completed, the microprocessor then determines a suitable output voltage. This determination can be based on an algorithm, which uses the incoming digital value in an equation to generate the output voltage. Such a method is useful when the output voltage has a linear or nearly linear relationship to the input voltage. In other scenarios, it may be advantageous to use a translation table to determine the appropriate output voltage. In other words, the incoming digital value is used to index a table, which provides the suggested output voltage.

Alternatively, in lieu of a microprocessor, especially in scenarios where the desired output voltage is proportional or linearly related to the input voltage, a circuit comprising passive and active components, such as resistors, capacitors, and opamps, can be employed.

Returning to FIG. 6, the output voltage produced by the microprocessor may be a PWM signal. In such a case, it may be necessary to convert this signal back to an analog value. In some embodiments, a low pass filter 617 may be used to convert a PWM signal to an analog voltage 618. An opamp 619 is then used to buffer this analog voltage 618. In other embodiments, the microprocessor may include a D/A converter and directly output an analog value.

As described above, in some embodiments, the output specification is 0-100 nA, with a 600-800 mV polarizing voltage. Therefore, the final stage of the circuit must convert an analog voltage, which is indicative of the desired current, into a current in the proper range. In this embodiment, the current is determined by measuring the voltage across resistor 634, which will be between 0 mV (no current) and the full polarizing voltage of 600-800 mV (maximum current). Opamp 632 simply buffers the voltage across resistor 634, and a resistor divider 633 may be used to reduce the voltage (if necessary) before it feeds into the negative input of opamp 630. In some embodiments, a circuit having a gain greater than one is used to amplify the voltage measured across resistor 634 such that the entire voltage range of the opamp 630 can be exploited. Such an embodiment may also increase the precision of the output.

The positive input of opamp 630 is fed by resistor divider 620. The output of opamp 630 is used to drive the gate of a FET transistor 631. This FET 631 has a variable resistance across its other two terminals, where that resistance is determined by the voltage applied to the gate of FET 631. The greater the voltage applied to the FET, the lower the resistance across its other two terminals. Thus, if the desired voltage, as applied to the positive terminal of opamp 630 is greater than the measured voltage, as applied to the negative terminal of opamp 630, the output of opamp 630 will increase, thereby lowering the resistance of FET 631. By reducing the resistance across FET 631, the current flow through resistor 634 increases.

As suggested above, other embodiments are also possible, including ones that do not include a microprocessor.

Furthermore, other variations of the circuit of FIG. 6 are possible. For example, if two output ports are desired, where both conform to the second specification, components 630-634 can be replicated to create a second output port. If an output port conforming to the first specification is desired, an opamp, configured as a buffer may be added near the input 610. Furthermore, if an output conforming to a third specification is desired, the applicable parts of the circuit shown in FIG. 6 can be duplicated. In certain embodiments, it may be necessary to replicate the microprocessor 615. However, the code executed by the microprocessor, or the lookup tables contained within may be modified.

While the above description illustrates a pharmaceutical system, the invention is not so limited. Other systems, such as those reactions using enzymes, nutriceuticals and pure chemical systems, can also utilize the present invention.

The terms and expressions which have been employed herein are used as terms of description and not of limitation, and there is no intention in the use of such terms and expressions of excluding any equivalents of the features shown and described (or portions thereof). It is also recognized that various modifications are possible within the scope of the claims. Other modifications, variations, and alternatives are also possible. Accordingly, the foregoing description is by way of example only and is not intended as limiting.

What is claimed is:

1. A method of utilizing a legacy controller with an oxygen sensor to control a reaction, comprising:
    locating said oxygen sensor in a reaction chamber, said oxygen sensor having an output, said sensor output being a voltage between 0 volts and 10 volts;

attaching the output of said oxygen sensor to an interface module;

using said oxygen sensor to monitor said reaction;

providing a legacy controller having two leads and a voltage source, where a polarizing voltage of 600 mV to 800 mV is created by said legacy controller between said leads using said voltage source, and where said leads are in electrical communication with said interface module;

using a circuit on said interface module, to convert said sensor output to a first digital value indicative of said sensor output;

using a processing unit to create a second digital value from said first digital value;

creating an analog voltage, based on said second digital value, said analog voltage indicative of a current to be provided to said legacy controller between said leads;

using said analog voltage to create an output voltage to be applied to a gate of a FET transistor, wherein said FET transistor comprises two other terminals disposed between said two leads, such that current between said leads flows through said FET transistor, and wherein said current through said leads is determined by said output voltage;

creating a current, in the range of 0 to 100 nA, between said two leads, by applying said output voltage to said gate of said FET transistor; and utilizing said legacy controller to control said reaction.

2. The method of claim 1, wherein said oxygen sensor comprises a fluorescence oxygen sensor.

3. The method of claim 1, wherein said interface module further comprises a second output port, said method further comprises using said interface module to transmit a voltage in the range of 0 volts to 10 volts.

4. The method of claim 1, wherein said interface module further comprises a second output port, said method further comprising using said interface module to transmit a current in the range of 0 to 100 nA on said second output port.

5. The method of claim 1, wherein said interface module further comprises a second output port, said method further comprising using said interface module to transmit information in conformance a third specification on said second output port.

6. The method of claim 1, wherein said second digital value is not linearly proportional to said first digital value.

7. A method of utilizing a legacy controller with an oxygen sensor to control a reaction, comprising:

locating said oxygen sensor in a reaction chamber, said oxygen sensor having an output, said sensor output being a current between 4 and 20 milliamps;

attaching the output of said oxygen sensor to an interface module;

using said oxygen sensor to monitor said reaction;

providing a legacy controller having two leads and a voltage source, where a polarizing voltage of 600 mV to 800 mV is created by said legacy controller between said leads using said voltage source, and where said leads are in electrical communication with said interface module;

using a circuit on said interface module, to convert said sensor output of said oxygen sensor to an input voltage, and to then convert said input voltage to a first digital value indicative of said sensor output;

using a processing unit to create a second digital value from said first digital value;

creating an analog voltage, based on said second digital value, said analog voltage indicative of a current to be provided to said legacy controller between said leads;

using said analog voltage to create an output voltage to be applied to a gate of a FET transistor, wherein said FET transistor comprises two other terminals disposed between said two leads, such that current between said leads flows through said FET transistor, and wherein said current through said leads is determined by said output voltage;

creating a current, in the range of 0 to 100 nA, between said two leads, by applying said output voltage to said gate of said FET transistor;

and utilizing said legacy controller to control said reaction.

8. The method of claim 7, wherein said oxygen sensor comprises a fluorescence oxygen sensor.

9. The method of claim 7, wherein said interface module further comprises a second output port, said method further comprises using said interface module to transmit a current in the range of 4 to 20 milliamps.

10. The method of claim 7, wherein said interface module further comprises a second output port, said method further comprising using said interface module to transmit a current in the range of 0 to 100 nA on said second output port.

11. The method of claim 7, wherein said second digital value is not linearly proportional to said first digital value.

* * * * *